United States Patent
Tokar et al.

(10) Patent No.: US 9,389,192 B2
(45) Date of Patent: Jul. 12, 2016

(54) ESTIMATION OF XRF INTENSITY FROM AN ARRAY OF MICRO-BUMPS

(71) Applicant: Jordan Valley Semiconductors Ltd., Migdal HaEmek, IL (US)

(72) Inventors: Alex Tokar, Haifa (IL); Alex Dikopoltsev, Haifa (IL); Isaac Mazor, Haifa (IL); Matthew Wormington, Littleton, CO (US)

(73) Assignee: BRUKER JV ISRAEL LTD., Migdal HaEmek (IL)

( * ) Notice: Subject to any disclaimer, the term of this patent is extended or adjusted under 35 U.S.C. 154(b) by 198 days.

(21) Appl. No.: 14/222,635

(22) Filed: Mar. 23, 2014

(65) Prior Publication Data

US 2014/0286473 A1     Sep. 25, 2014

Related U.S. Application Data

(60) Provisional application No. 61/804,667, filed on Mar. 24, 2013.

(51) Int. Cl.
*G01N 23/223* (2006.01)

(52) U.S. Cl.
CPC ........ *G01N 23/223* (2013.01); *G01N 2223/076* (2013.01)

(58) Field of Classification Search
CPC .......... G01N 2223/076; G01N 23/223; G01N 23/22; G01N 23/2206; G01N 2223/646
See application file for complete search history.

(56) References Cited

U.S. PATENT DOCUMENTS

| | | | |
|---|---|---|---|
| 3,256,431 A | 6/1966 | Frazer | |
| 3,581,087 A | 5/1971 | Brinkerhoff | |
| 3,919,548 A | 11/1975 | Porter | |
| 3,980,568 A | 9/1976 | Pitchford et al. | |
| 3,984,680 A | 10/1976 | Smith | |
| 4,048,496 A | 9/1977 | Albert | |
| 4,085,329 A | 4/1978 | McCoy et al. | |
| 4,169,228 A | 9/1979 | Briska et al. | |

(Continued)

FOREIGN PATENT DOCUMENTS

| | | |
|---|---|---|
| JP | 6186344 A | 7/1994 |
| JP | 06273146 A | 9/1994 |

(Continued)

OTHER PUBLICATIONS

Boer et al., "How Accurate is the Fundamental Parameter Approach? XRF Analysis of Bulk and Multilayer Samples", X-RAY Spectrometry, vol. 22, pp. 33-38, year 1993.

(Continued)

*Primary Examiner* — Hoon Song
(74) *Attorney, Agent, or Firm* — D. Kligler IP Services Ltd.

(57) ABSTRACT

A method for inspection includes capturing an optical image of one or more features on a surface of a sample and irradiating an area of the sample containing at least one of the features with an X-ray beam. An intensity of X-ray fluorescence emitted from the sample in response to the irradiating X-ray beam is measured. The optical image is processed so as to extract geometrical parameters of the at least one of the features and to compute a correction factor responsively to the geometrical parameters. The correction factor is applied to the measured intensity in order to derive a property of the at least one of the features.

17 Claims, 7 Drawing Sheets

(56) References Cited

U.S. PATENT DOCUMENTS

| | | |
|---|---|---|
| 4,446,568 A | 5/1984 | Williams et al. |
| 4,551,905 A | 11/1985 | Chao et al. |
| 4,590,603 A | 5/1986 | Relihan et al. |
| 4,710,259 A | 12/1987 | Howe et al. |
| 4,718,075 A | 1/1988 | Horn |
| 4,725,963 A | 2/1988 | Taylor et al. |
| 4,847,882 A | 7/1989 | Knoth et al. |
| 4,852,135 A | 7/1989 | Anisovich et al. |
| 4,916,720 A | 4/1990 | Yamamoto et al. |
| 4,989,226 A | 1/1991 | Woodbury et al. |
| 5,151,588 A | 9/1992 | Kiri et al. |
| 5,365,563 A | 11/1994 | Kira et al. |
| 5,385,867 A | 1/1995 | Kumakhov |
| 5,425,066 A | 6/1995 | Takahashi et al. |
| 5,481,109 A | 1/1996 | Ninomiya et al. |
| 5,497,008 A | 3/1996 | Kumakhov |
| 5,574,284 A | 11/1996 | Farr |
| 5,619,548 A | 4/1997 | Koppel |
| 5,740,226 A | 4/1998 | Komiya et al. |
| 5,742,658 A | 4/1998 | Tiffin et al. |
| 5,778,039 A | 7/1998 | Hossain et al. |
| 5,877,498 A | 3/1999 | Sugimoto et al. |
| 5,893,758 A | 4/1999 | Sandhu et al. |
| 5,900,645 A | 5/1999 | Yamada |
| 5,909,276 A | 6/1999 | Kinney et al. |
| 5,923,720 A | 7/1999 | Barton et al. |
| 5,937,026 A | 8/1999 | Satoh |
| 5,937,027 A | 8/1999 | Thevenin et al. |
| 5,949,847 A | 9/1999 | Terada et al. |
| 5,963,329 A | 10/1999 | Conrad et al. |
| 6,001,736 A | 12/1999 | Kondo et al. |
| 6,040,095 A | 3/2000 | Enichen et al. |
| 6,041,095 A | 3/2000 | Yokhin |
| 6,041,098 A | 3/2000 | Touryanski et al. |
| 6,108,398 A | 8/2000 | Mazor et al. |
| 6,173,036 B1 | 1/2001 | Hossain et al. |
| 6,192,103 B1 | 2/2001 | Wormington et al. |
| 6,226,347 B1 | 5/2001 | Golenhofen |
| 6,226,349 B1 | 5/2001 | Schuster et al. |
| 6,266,389 B1 | 7/2001 | Murayama et al. |
| 6,345,086 B1 | 2/2002 | Ferrandino et al. |
| 6,351,516 B1 | 2/2002 | Mazor et al. |
| 6,381,303 B1 | 4/2002 | Vu et al. |
| 6,389,102 B2 | 5/2002 | Mazor et al. |
| 6,453,002 B1 | 9/2002 | Mazor et al. |
| 6,453,006 B1 | 9/2002 | Koppel et al. |
| 6,507,634 B1 | 1/2003 | Koppel et al. |
| 6,512,814 B2 | 1/2003 | Yokhin et al. |
| 6,556,652 B1 | 4/2003 | Mazor et al. |
| 6,639,968 B2 | 10/2003 | Yokhin et al. |
| 6,643,354 B2 | 11/2003 | Koppel et al. |
| 6,680,996 B2 | 1/2004 | Yokhin et al. |
| 6,704,661 B1 | 3/2004 | Opsal et al. |
| 6,711,232 B1 | 3/2004 | Janik |
| 6,744,850 B2 | 6/2004 | Fanton et al. |
| 6,744,950 B2 | 6/2004 | Aleksoff |
| 6,750,952 B2 | 6/2004 | Grodnensky et al. |
| 6,754,304 B1 | 6/2004 | Kumakhov |
| 6,754,305 B1 | 6/2004 | Rosencwaig et al. |
| 6,771,735 B2 | 8/2004 | Janik et al. |
| 6,810,105 B2 | 10/2004 | Nasser-Ghodsi et al. |
| 6,823,043 B2 | 11/2004 | Fewster et al. |
| 6,879,051 B1 | 4/2005 | Singh et al. |
| 6,890,575 B2 | 5/2005 | Beauregard et al. |
| 6,891,627 B1 | 5/2005 | Levy et al. |
| 6,895,075 B2 | 5/2005 | Yokhin et al. |
| 6,947,520 B2 | 9/2005 | Yokhin et al. |
| 6,977,986 B1 | 12/2005 | Beanland et al. |
| 7,023,954 B2 | 4/2006 | Rafaeli et al. |
| 7,062,013 B2 | 6/2006 | Berman et al. |
| 7,068,753 B2 | 6/2006 | Berman et al. |
| 7,071,007 B2 | 7/2006 | Tseng et al. |
| 7,103,142 B1 | 9/2006 | Agnihotri et al. |
| 7,110,491 B2 | 9/2006 | Mazor et al. |
| 7,120,228 B2 | 10/2006 | Yokhin et al. |
| 7,130,376 B2 | 10/2006 | Berman et al. |
| 7,183,547 B2 | 2/2007 | Yun et al. |
| 7,245,695 B2 | 7/2007 | Mazor et al. |
| 7,551,719 B2 | 6/2009 | Yokhin et al. |
| 7,600,916 B2 | 10/2009 | Yokhin et al. |
| 7,649,978 B2 | 1/2010 | Mazor et al. |
| 7,653,174 B2 | 1/2010 | Mazor et al. |
| 7,804,934 B2 | 9/2010 | Agnihotri et al. |
| 7,968,444 B2 | 6/2011 | Luo et al. |
| 2001/0028699 A1 | 10/2001 | Iwasaki |
| 2001/0043668 A1 | 11/2001 | Hayashi et al. |
| 2002/0097837 A1 | 7/2002 | Fanton et al. |
| 2002/0110218 A1 | 8/2002 | Koppel et al. |
| 2003/0012337 A1 | 1/2003 | Fewster et al. |
| 2003/0128809 A1 | 7/2003 | Umezawa et al. |
| 2003/0157559 A1 | 8/2003 | Omote et al. |
| 2004/0052330 A1 | 3/2004 | Koppel et al. |
| 2004/0109531 A1 | 6/2004 | Yokhin et al. |
| 2004/0131151 A1 | 7/2004 | Berman et al. |
| 2004/0156474 A1 | 8/2004 | Yokhin et al. |
| 2004/0218717 A1 | 11/2004 | Koppel et al. |
| 2004/0267490 A1 | 12/2004 | Opsal et al. |
| 2005/0282300 A1 | 12/2005 | Yun et al. |
| 2006/0062350 A1 | 3/2006 | Yokhin et al. |
| 2006/0227931 A1 | 10/2006 | Mazor et al. |
| 2006/0274886 A1 | 12/2006 | Mazor et al. |
| 2008/0021665 A1 | 1/2008 | Vaughnn |
| 2008/0049895 A1 | 2/2008 | Agnihotri et al. |
| 2008/0095309 A1* | 4/2008 | Puusaari ............ G01N 23/223 378/4 |
| 2008/0159475 A1 | 7/2008 | Mazor et al. |
| 2013/0039460 A1* | 2/2013 | Levy .................. G01N 21/211 378/44 |
| 2013/0089178 A1 | 4/2013 | Mazor et al. |

FOREIGN PATENT DOCUMENTS

| | | |
|---|---|---|
| JP | 2006283585 A | 10/1994 |
| JP | 07019844 A | 1/1995 |
| JP | 7128259 A | 5/1995 |
| JP | 09308339 A | 12/1997 |
| JP | 10048398 A | 2/1998 |
| JP | 10318949 A | 12/1998 |
| JP | 2004003959 A | 1/2004 |
| JP | 2004151004 A | 5/2004 |
| WO | 92/08235 A1 | 5/1992 |

OTHER PUBLICATIONS

U.S. Appl. No. 13/647,408 Office Action dated Oct. 30, 2014.

Singer, "Copper CMP: Taking aim at Dishing", Semiconductor International (www.reed-electronics.com/semiconductor/), 4 pages, Oct. 1, 2004.

Reed Electronics Group, Semiconductor International, "Webcast Equipment Auction" (www.reed-electronics.com/semiconductor/), 2 pages, Dec. 15, 2005.

Dane et al., "Application of Genetic Algorithms for Characterization of Thin Layered Materials by Glancing Incidence X-Ray Reflectometry", Physica B 253, pp. 254-268, Feb. 26, 1998.

Kozaczek et al., "X-Ray Diffraction Metrology for 200 mm Process Qualification and Stability Assessment", Advanced Metallization Conference, Montreal, Canada, 6 pages, Oct. 8-11, 2001.

Powell et al., "X-Ray Diffraction and Reflectivity Characterization of SiGe Superlattice Structures", Semiconductor Science and Technology Journal, vol. 7, No. 5, pp. 627-631, United Kingdom, 1992.

Neissendorfer et al., "The Energy—Dispersive Reflectometer / Diffractometer at Bessy-I", Measurement Science and Technology Journal, vol. 10, No. 5, pp. 354-361, year 1999.

Ulyanenkov, "Introduction to High Resolution X-Ray Diffraction", Workshop on X-Ray Characterization to Thin Layers, 50 pages, Uckley, May 21-23, 2003.

Huang et al., "Characterization of Single and Multiple—Layer Films by X—Ray Reflectometry", Advances in X-Ray Analysis, vol. 35, pp. 137-142, New York, USA, 1992.

EX-6500 Advanced EDXRF Spectrometer Manufactures by Jordan Valley Semiconductors, 2 pages, year 2000.

(56) References Cited

OTHER PUBLICATIONS

Lengeler, "X-Ray Reflection, a New Tool for Investigating Layered Structures and Interfaces", Advances in X-Ray Analysis, Plenum Press, vol. 35, pp. 127-135, New York, USA, 1992.
Lankosz et al., "Research in Quantitative X-Ray Fluorescence Microanalysis of Patterned This Films", Advances in X-Ray Analysis, vol. 43, pp. 497-503, year 1999.
Parrill et al., "GISAXS—Glancing Incidence Small Angle X-Ray Scattering", Journal de Physique IV, supplement to Journal de Physique I, vol. 3, pp. 411-417, Dec. 1993.
Bowen et al., "X-Ray Metrology by Diffraction and Reflectivity", 2000 International Conference on Characterization and Metrology for ULSI Technology, NIST, Gaithersburg, Maryland, USA, pp. 570-579, Jun. 26-29, 2000.
Naudon et al., "New Apparatus for Grazing X—Ray Reflectometry in the Angle—Resolved Dispersive Mode", Journal of Applied Crystallography, vol. 22, pp. 460-464, year 1989.
X-Ray Optical Systems, Inc., "Monolithic Polycapillary Lens Information", Albany, USA, 1 page, Dec. 29, 1998.
Markowicz et al., "Quantification in XRF Analysis of Intermediate—Thickness Samples", Handbook of X-Ray Spectrometry, 2nd edition, chapter 6, pp. 408-431, Antwerp, Belgium, CRC Press 2001.
U.S. Appl. No. 11/018,352, Office Action dated Feb. 8, 2006.
U.S. Appl. No. 11/889,337, Office Action dated Jul. 24, 2008.
U.S. Appl. No. 11/018,352, Office Action dated Oct. 24, 2005.
U.S. Appl. No. 11/487,433, Office Action dated May 29, 2008.
U.S. Appl. No. 12/003,215, Office Action dated Apr. 1, 2009.
U.S. Appl. No. 11/103,071, Office Action dated Oct. 5, 2006.
U.S. Appl. No. 09/028,588, Office Action dated Jun. 4, 1999.
Jones et al., "Small Angle X-Ray Scattering for sub-100 nm Pattern Characterization", Journal of Applied Physics, vol. 83, No. 19, pp. 4059-4061, Nov. 10, 2003.
Hu et al., "Small Angle X-Ray Scattering Metrology for Sidewall Angle and Cross Section of Nanometer Scale Line Gratings", Journal of Applied Physics, vol. 96, No. 4, pp. 1983-1987, Aug. 15, 2004.
Wu et al., "Small Angle Neutron Scattering Measurements of Nanoscale Lithographic Features", Polymer Preprints, vol. 42, No. 1, pp. 265-266, year 2001.

Kojima et al., "Structural Characterization of Thin Films by X-Ray Reflectivity", Rigaku Journal, vol. 16, No. 2, pp. 31-41, year 1999.
X-Ray Optical Systems, Inc., "Micro X-Ray Fluorescence with Focusing Polycapillary Optics", Application Note 102, 2 pages, USA, Jun. 12, 2002.
Guerault, "Specular Reflectivity and Off-Specular Scattering: Tools for Roughness Investigation", Institute Voor Kern—en Stralingsfysica, 15 pages, Dec. 15, 2000.
Wiener et al., "Characterization of Titanium Nitride Layers by Grazing—Emission X-Ray Fluorescence Spectrometry", Applied Surface Science, vol. 125, pp. 129-136, Elsevier Science B.V., year 1999.
Hayashi et al., "Refracted X-Rays Propagating Near the Surface Under Grazing Incidence Condition", Spectrochimica Acta, Part B 54, pp. 227-230, year 1999.
Di-Fonzo et al., "Non-Destructive Determination of Local Strain with 100—Nanometre Spatial Resolution", Letters to Nature, vol. 403, pp. 638-640, Feb. 10, 2000.
Agnihotri, U.S. Appl. No. 11/610,174, "Accurate Measurement of Layer Dimensions using XRF", filed Dec. 13, 2006 (abandoned).
Japan Patent Application 2007-340602, Office Action dated Apr. 24, 2012.
Leng et al., "Simultaneous Measurement of Six Layers in a Silicon on Insulator Film Stack using Spectrophotometry and Beam Profile Reflectometry", Journal of Applied Physics, vol. 81, No. 8, pp. 3570-3578, Apr. 15, 1997.
Boer, "Calculation of X-Ray Fluorescence Intensities from Bulk and Multilayer Samples", X-Ray Spectrometry, vol. 19, pp. 145-154, 1990.
Mantler, "X-ray fluorescence analysis of multiple-layer films", Analytica chimica acta, vol. 188, pp. 25-35, 1986.
Patterson, "Transforming mobile electronics with copper pillar interconnect", Advancing microelectronics, vol. 39, No. 3, pp. 18-24, May/Jun. 2012.
Beckhoff et al, "Handbook of Practical X-Ray Fluorescence Analysis", Springer-Verlag, Berlin, Heidelberg , pp. 1-30, 2006.
U.S. Appl. No. 13/647,408 Official Action dated Jul. 25, 2014.
U.S. Appl. No. 13/647,408 Office Action dated Jul. 8, 2015.

* cited by examiner

ESTIMATION OF XRF INTENSITY FROM AN ARRAY OF MICRO-BUMPS

CROSS-REFERENCE TO RELATED APPLICATIONS

This application claims the benefit of U.S. Provisional Patent Application 61/804,667, filed Mar. 24, 2013, which is incorporated herein by reference.

FIELD OF THE INVENTION

The present invention relates generally to X-ray inspection systems and methods, and specifically to inspection of small features using X-ray fluorescence.

BACKGROUND

X-ray fluorescence (XRF) measurement, and specifically X-ray microfluorescence (i.e., X-ray fluorescence using focused excitation beams of small diameter, such as less than 100 µm), is commonly used in testing semiconductor wafers. XRF itself is a well-known technique for determining the elemental composition and other properties, such as thickness, of a sample. XRF analyzers generally include an X-ray source, which irradiates the sample with sufficient energy to excite X-ray fluorescence from the elements of interest within the sample, and an X-ray detector, for detecting the X-ray fluorescence emitted by the sample in response to the irradiation. Each element in the sample emits X-ray fluorescence in energy bands that are characteristic of the element. The detected X-ray fluorescence is analyzed to find the energies or, equivalently, the wavelengths of the detected photons and the number of emitted photons (intensity) as a function of energy or wavelength, and the qualitative and/or quantitative composition of the sample is determined based on this analysis.

U.S. Pat. No. 6,108,398, for example, whose disclosure is incorporated herein by reference, describes an XRF analyzer and a method for analyzing a sample. The analyzer includes an X-ray beam generator, which generates an X-ray beam incident at a spot on the sample and creates a plurality of fluorescent X-ray photons. An array of semiconductor detectors is arranged around the spot so as to capture the fluorescent X-ray photons. The analyzer produces electrical pulses suitable for analysis of the sample.

The use of X-ray microfluorescence for testing semiconductor wafers is described in U.S. Pat. No. 6,351,516, whose disclosure is incorporated herein by reference. This patent describes a non-destructive method for testing the deposition and/or the removal of a material within a recess on the surface of a sample. An excitation beam is directed onto a region of the sample in a vicinity of the recess, and an intensity of X-ray fluorescence emitted from the region is measured. A quantity of the material that is deposited within the recess is determined responsively to the measured intensity.

U.S. Pat. No. 7,653,174, whose disclosure is incorporated herein by reference, describes methods for inspection of small features using X-ray fluorescence. These methods are based on measuring the intensity of X-ray emission from a sample at multiple different locations of an irradiating X-ray beam relative to a target feature on the sample. The corresponding intensity measurements are processed in order to give an adjusted value of the emission, which is more accurately indicative of characteristics (such as thickness) of the feature.

U.S. Patent Application Publication 2013/0089178, whose disclosure is incorporated herein by reference, describes a method for inspection of a feature formed on a semiconductor wafer, which includes a volume containing a first material and a cap made of a second material, different from the first material, that is formed over the volume. The feature is irradiated with a focused beam, and one or more detectors positioned at different angles relative to the feature are used to detect X-ray fluorescent photons that are emitted by the first material in response to the irradiating beam and pass through the cap before striking the detectors. Signals output by the one or more detectors at the different angles in response to the detected photons are processed in order to assess a quality of the cap.

SUMMARY

Embodiments of the present invention that are described hereinbelow provide improved methods and apparatus for inspection of small structures using X-ray fluorescence.

There is therefore provided, in accordance with an embodiment of the present invention, a method for inspection, which includes capturing an optical image of one or more features on a surface of a sample. An area of the sample containing at least one of the features is irradiated with an X-ray beam, and an intensity of X-ray fluorescence emitted from the sample in response to the irradiating X-ray beam is measured. The optical image is processed so as to extract geometrical parameters of the at least one of the features and to compute a correction factor responsively to the geometrical parameters. The correction factor is applied to the measured intensity in order to derive a property of the at least one of the features.

In some embodiments, irradiating the area includes focusing an X-ray beam onto the surface of the sample, and wherein the optical image is captured by a microscope that is aligned with the focused X-ray beam. Additionally or alternatively, measuring the intensity of the X-ray fluorescence includes detecting fluorescent X-rays using one or more detectors positioned at respective angles relative to the feature, and processing the optical image includes computing the correction factor responsively to respective angular slopes between the one or more detectors and the at least one of the features.

In the disclosed embodiments, applying the correction factor includes deriving at least one property of the at least one of the features, selected from a group of properties consisting of a composition and a size parameter of the at least one of the features.

In one embodiment, processing the optical image includes recognizing that the irradiated area of the sample contains a plurality of the features, and computing the correction factor so as to enable the property of a single feature to be derived from the intensity of the X-ray fluorescence that is received from the plurality of the features. Additionally or alternatively, processing the optical image includes recognizing that the at least one of the features has a shape that differs from a specified reference shape, and computing the correction factor so as to correct the intensity of the X-ray fluorescence for the shape of the at least one of the features.

Typically, processing the optical image includes computing the correction factor by integrating an expected X-ray emission intensity over the irradiated area of the sample using the extracted geometrical parameters of the at least one of the features.

In a disclosed embodiment, the sample is a wafer, and the features include bumps formed on the surface of the wafer, and applying the correction factor includes assessing a quality of the bumps.

There is also provided, in accordance with an embodiment of the present invention, inspection apparatus, including a microscope, which is configured to capture an optical image of one or more features on a surface of a sample, and an X-ray source, which is configured to irradiate an area of the sample containing at least one of the features with an X-ray beam. One or more detectors are positioned to measure an intensity of X-ray fluorescence emitted from the sample in response to the irradiating X-ray beam. A signal analyzer is configured to process the optical image so as to extract geometrical parameters of the at least one of the features, to compute a correction factor responsively to the geometrical parameters, and to apply the correction factor to the measured intensity in order to derive a property of the at least one of the features.

The present invention will be more fully understood from the following detailed description of the embodiments thereof, taken together with the drawings in which:

DETAILED DESCRIPTION OF EMBODIMENTS

Figure 1:
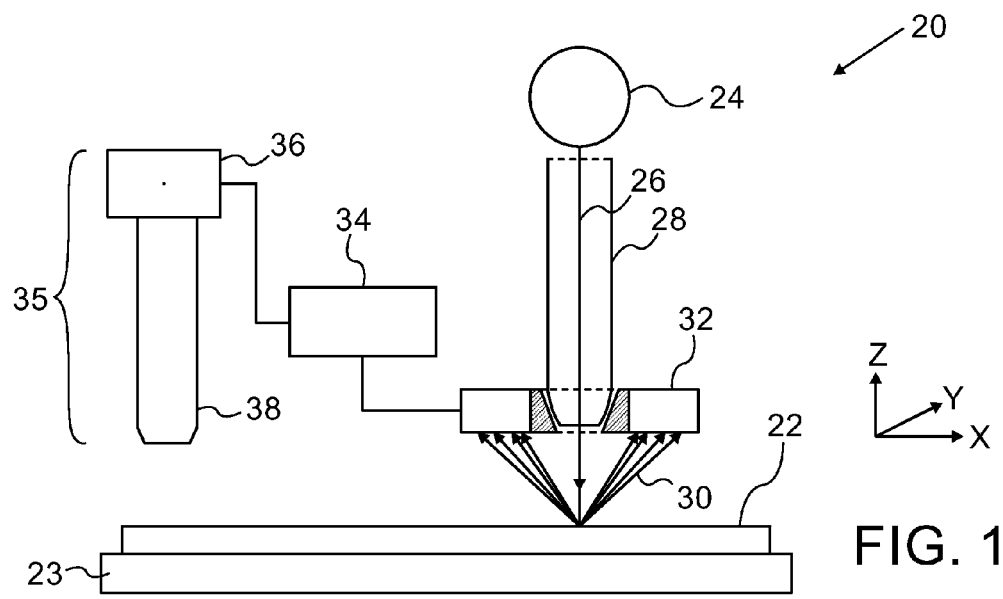
FIG. 1 is a schematic illustration of a system for X-ray microfluorescence measurement, in accordance with an embodiment of the present invention.

Embodiments of the present invention that are described herein are directed to measurement of composition and size parameters, such as thickness, of small features using X-ray microfluorescence. In the context of the present patent application, "small" refers to features of a sample, such as elements of an integrated circuit on a semiconductor wafer, whose dimensions are comparable to or less than the diameter of the X-ray spot on the surface of the sample, which is typically less than 100 µm. In an integrated circuit device, the values of these parameters can be critical to the quality and performance of the device, but they are otherwise difficult or impossible to measure accurately and non-destructively. The methods of micro-XRF that are described hereinbelow are directed particularly to evaluation of the composition and quality of solder bumps that are formed on a wafer. (Such bumps, which may alternatively be referred to as micro-bumps, are commonly used in attaching a semiconductor chip to another semiconductor chip or a circuit substrate after production of the chip is complete.) The principles of the present invention, however, may similarly be applied in inspection of small features of other sorts, both on semiconductor wafers and on other sorts of samples.

The embodiments disclosed herein address problems encountered in the practical application of XRF-based methods in metrology of small bumps and other microscopic features. Problems of this sort occur in the use of the types of micro-XRF apparatus and methods that are described in the patents cited above; and the disclosed embodiments take this type of system as an operational example. In these embodiments, an optical microscope, with suitable hardware and software for image acquisition and processing, is added to the system and used in combination with micro-XRF apparatus to enhance the accuracy of the XRF-based analysis. Alternatively, the principles of the present invention may be applied, mutatis mutandis, using other systems with suitable XRF and optical measurement capabilities.

When an X-ray beam is focused onto an array of small bumps, it is ideally desirable, for purposes of measurement accuracy, that the X-ray beam impinge squarely on one of the bumps, and only on that bump. In practice, however, such alignment cannot be achieved if the beam size on the sample is comparable to the bump being measured, and the beam tends to "spill off" the bumps. In the case of low-density bump arrays, in which the bump-to-bump distance is much greater than the beam spot size, only a fraction of the incident intensity may actually excite fluorescence of the feature of interest. In the case of dense bump arrays, in which the bump-to-bump distance is less than or on the order of the beam spot size, the beam may fall partially or totally onto adjacent bumps. In either case, it is desirable that the fluorescent intensity be corrected to give an accurate measurement of the properties of the bump of interest.

If the arrangement of bumps and measurement setup are known precisely in advance, the measurement system can be adjusted and calibrated precisely before each measurement begins. When a large number of different wafers, with different arrangements of bumps, are to be tested, however (such as in a semiconductor foundry), a new recipe must be devised and verified for each product. This approach is time-consuming and error-prone.

Embodiments of the present invention that are described herein resolve these issues by dynamically correcting for environmental influences and other variations in XRF measurement conditions. In these embodiments, an optical image of the measurement area is processed during the measurement, using only minimal a priori information (such as the beam size and feature size and shape). This information may be input by a user of the measurement system or, alternatively or additionally, may be calibrated automatically by the system. The image processing results are applied in correcting the XRF measurements.

Specifically, in the disclosed embodiments, an optical microscope, whose position is known accurately relative to the X-ray beam, captures a high-resolution image of the feature of interest, such as a bump or array of bumps. This image is processed and converted to a map of features using methods of image segmentation and pattern recognition that are known in the art. Geometrical parameters of the features in the map, such as their size, shape, and distribution relative to the X-ray beam area, are used to correct the measured XRF intensity for misalignment and other variations in bump characteristics and X-ray test conditions.

In one embodiment, the geometrical parameters are approximated based on the overlap of the X-ray beam intensity with a model of bump characteristics. The correction may be based, for example, on numerical integration (summation) of the overlap between the beam profile and the region(s) occupied by the bumps. Additionally or alternatively, the expected XRF emission profile may be estimated by simulation of the physical properties of the bump and the measurement system, and this profile may then be applied in correcting the XRF measurement results. Both of these approaches are described in greater detail hereinbelow.

FIG. 1 is a schematic illustration of an X-ray microfluorescence analysis system 20, in accordance with an embodiment of the present invention. Aspects of system 20 are described in detail in the above-mentioned U.S. Pat. No. 6,108,398. System 20 is arranged to examine a semiconductor wafer 22 (or another sample), in order to measure properties of features formed on the wafer during the fabrication process, using methods described hereinbelow. For example, system 20 may measure and analyze the properties of an irradiated spot including bump composition and height, as well as the thickness of under-bump metal (UBM) layers.

System 20 comprises an excitation source, such as an X-ray tube 24, driven by a high-voltage power supply, as is known in the art. The X-ray tube emits an X-ray beam 26 having a suitable energy range and power flux into X-ray optics 28. The optics may comprise a polycapillary array, for example. Optics 28 focus the X-ray beam onto a small region, typically a spot on the order of 10-20 µm in diameter, on the surface of wafer 22. The irradiated region emits fluorescent X-rays 30, which are captured by an array of detectors 32 arranged around the irradiated region and may be angled toward it. The detectors may comprise any suitable type of X-ray detectors, such as Si(Li) (lithium-drifted silicon) detectors or silicon drift detectors (SDDs), which generate pulses whose amplitude is proportional to the energy of the incident X-ray photons. In response to the captured photons, detectors 32 generate electrical signals, which are conveyed to a signal analyzer 34.

Alternatively, other types of X-ray fluorescence analyzers known in the art, comprising any suitable excitation source, power source, focusing optics and detection system, may be used for implementing the methods described herein. For example, a single detector and/or other suitable focusing and detection configurations may be used.

Signal analyzer 34 typically comprises, in part, an energy-dispersive pulse processor, as is known in the art, coupled to a digital processor, which computes the intensity spectrum of the X-ray photons captured by the detectors. Typically, the signal analyzer is configured as a multi-channel analyzer (MCA), which counts the fluorescent photons as a function of photon energy. Alternatively, detectors 32 and signal analyzer 34 may be configured as a wavelength-dispersive detection and processing system.

The digital processor in signal analyzer 34 typically comprises a general-purpose computer, which performs the digital processing functions of system 20 under the control of suitable software. The software may be downloaded to the processor in electronic form, over a network, for example, or it may alternatively be provided on tangible, non-transitory media, such as optical, magnetic or electronic memory media.

Typically, wafer 22 is mounted on a movable platform, such as a motion stage 23, so as to enable the wafer to be translated and/or rotated with respect to X-ray beam 26 and detectors 32. Alternatively, the wafer may be mounted on a suitable stationary fixture while tube 24, optics 28 and detectors 32 are moved, so that the X-ray beam can be directed at different locations on the wafer.

System 20 may be further configured to capture and process X-rays scattered from wafer 22 by other mechanisms, such as reflection, diffraction, and/or small-angle scattering. Multi-function systems of this sort are described, for example, in U.S. Pat. Nos. 6,381,303 and 6,895,075 and 7,551,719, whose disclosures are incorporated herein by reference.

An optical microscope 35, comprising a suitable lens 38 and an image sensor 36, is aligned with irradiating X-ray beam 26, typically at a known spatial offset. The offset is precisely measured and calibrated before use, so that motion stage 23 on which sample 22 is mounted can translate the measurement point between the optical focus and the X-ray focus with the required accuracy. Analyzer 34 processes the optical images generated by the image sensor in order identify the bumps, measure their diameters and locations, and compute correction factors as described below. The stages of bump identification and diameter measurement may be carried out using methods of image processing that are known in the art and are available as utilities in standard software packages. One such package that may be used in this context, for example, is the Matrox Imaging Library (Matrox Electronic Systems Ltd., Dorval, Quebec).

XRF is generally a calibrated technique, which relies on standards—which may take the form, in the present case, of one or more bumps of known height or thin-films of known thickness. Bumps can be of various sizes and shapes. They can also be laid out in various arrays and configurations. Yet practically speaking, it is desirable to use the same set of standards for any size, shape and layout. Therefore, the standards used in the present embodiment are flat samples with lateral dimensions sufficiently large to be considered infinite.

To provide accurate measurement of bump parameters, the measured XRF intensity ($I^{measured}$) is corrected by two factors, $C_n$ and $C_s$:

$$I_{sb}^{true} = C_n * C_s * I^{measured} \tag{1}$$

$C_n$—This factor takes into account the influence of neighboring bumps. Optical pattern recognition is used, as explained below, to account for this influence. This use of pattern recognition and the resulting input to correct measured X-ray intensity and derive accurate bump parameters is a key feature of the present embodiment. If the distance between bumps is very large, $C_n$->1 (meaning that all X-rays sensed by the X-ray detectors are emitted from a single bump).

$C_s$—This factor takes into account that the shape of the bump differs from a certain specified reference shape, meaning in the present case that the bump is finite and non-planar. For example, pre-reflow (pre-melted) bumps are typically flat, while post-reflow (re-melted) bumps have curved surfaces, as dictated by thermodynamics. $C_s$ may be calculated based on user input of dimensions and process step (including nominal radii, assuming elliptical shape). Alternatively or additionally, microscope 35 may be configured to extract three-dimensional image information, using techniques such as stereoscopic imaging or confocal microscopy, and analyzer 34 may then estimate the bump dimensions and shape based on this information. If a bump is much larger than the X-ray beam diameter, so that it becomes effectively infinite in size, $C_s$->1 (and $C_n$ will be equal to 1, as well).

Figure 2A:
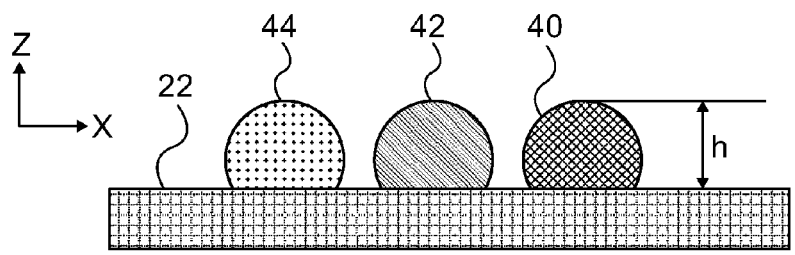
FIGS. 2A and 2B are schematic sectional and top views, respectively, of an array of micro-bumps on a semiconductor wafer, illustrating principles of inspection of the micro-bumps in accordance with an embodiment of the present invention.
Figure 2B:
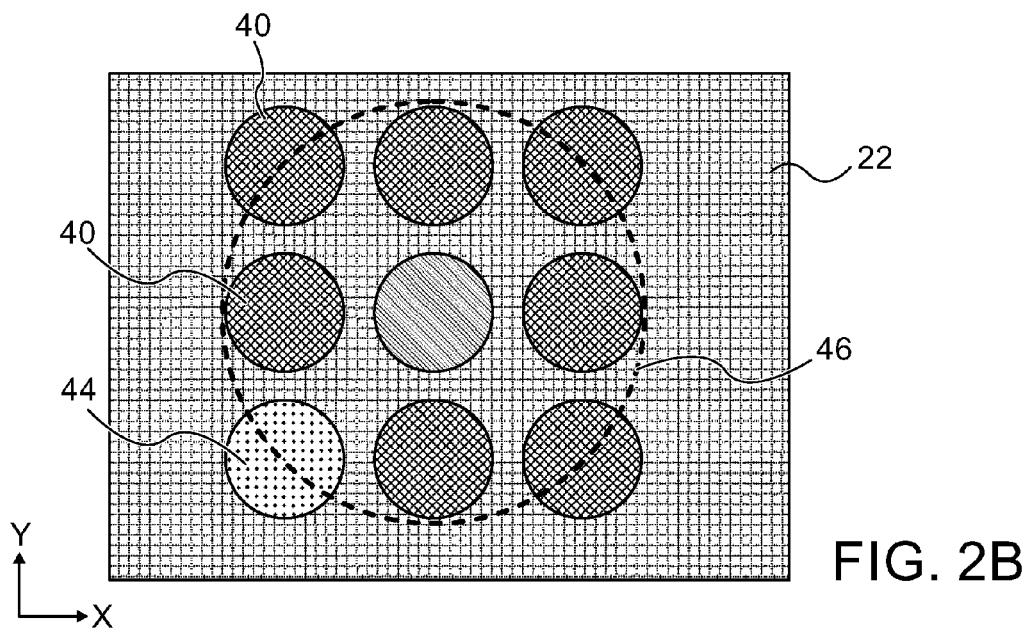

FIGS. 2A and 2B schematically illustrate a dense array of bumps 40, 42, 44, in sectional and top views respectively, which is irradiated by an X-ray beam 46, in accordance with an embodiment of the present invention. The height and composition of a single bump are to be measured accurately, using system 20. Different bumps 40, 42 and 44 are assumed to be subject to different environmental influences, which may alter the properties of these bumps with respect to XRF measurement. The methods described herein correct for the alignment of X-ray beam 46 relative to the bump array so that properties of central bump 42 in the array can be derived from the X-ray measurement results, notwithstanding possible environmental non-uniformities.

Figure 3A:
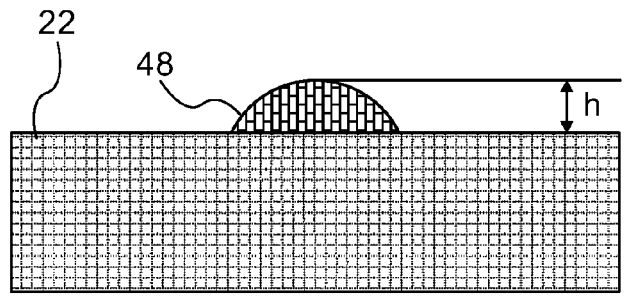
FIGS. 3A-3D are schematic sectional views of micro-bumps on a semiconductor wafer, illustrating principles of inspection of the micro-bumps in accordance with an embodiment of the present invention.
Figure 3B:
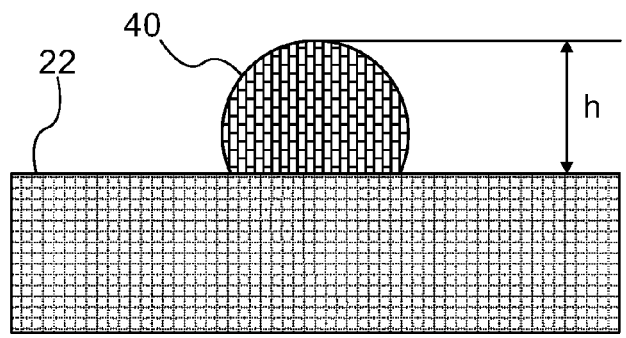
Figure 3C:
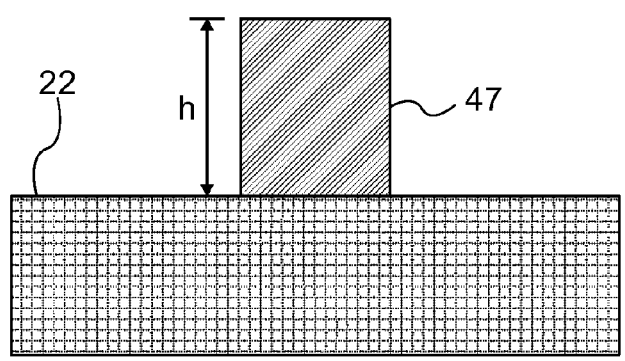
Figure 3D:
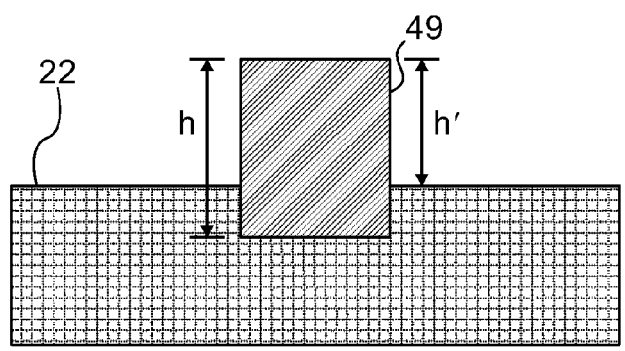

FIGS. 3A-3D are schematic sectional views of various bumps, illustrating another feature of the bumps that is taken into account by analyzer 34: The height h of a bump 48 in FIG. 3A, for example, is less than the bump radius, while that of bump 40 in FIG. 3B is greater than the bump radius. The significance of these dimensions is seen in the description that follows. As another example, FIG. 3C shows a cylindrical feature 47 that is typical of solder bumps prior to reflow, while FIG. 3D shows a partially embedded feature 49, such as a copper pillar bump recessed into wafer 22. The methods that are described herein enable system 20 to measure the actual height h of such features. By contrast, when optical measurement methods that are known in the art are applied to the sort of feature 49 that is shown in FIG. 3D, only the height by which the feature protrudes above the surface of the substrate, h', is typically measured.

Figure 4:
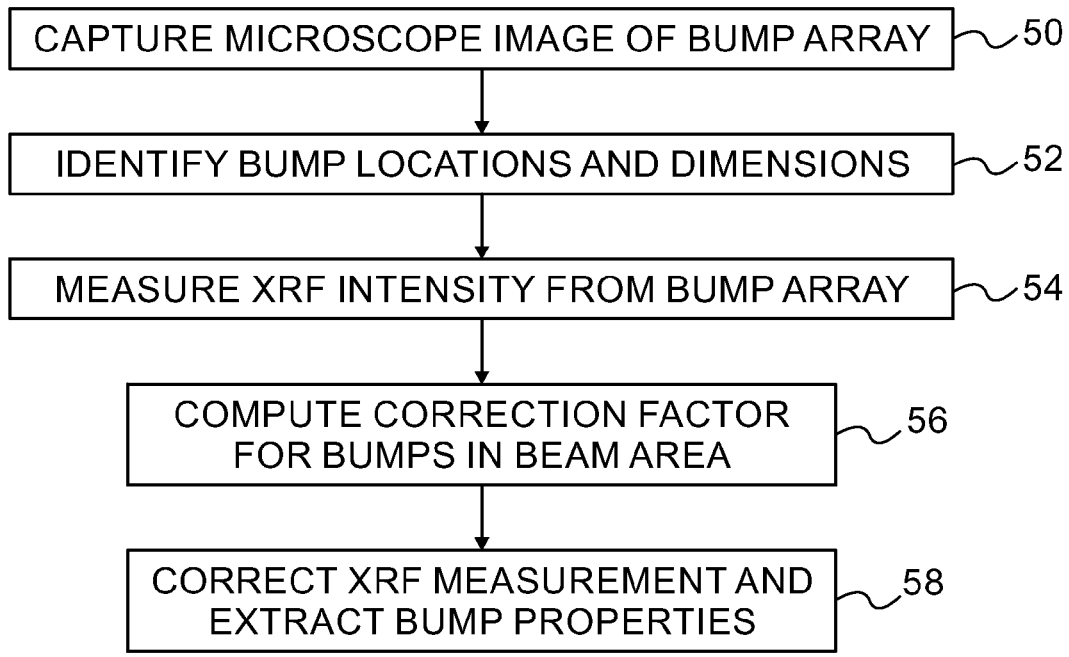
FIG. 4 is a flow chart, which schematically illustrates a method for inspection of micro-bumps on a wafer, in accordance with an embodiment of the present invention.

FIG. 4 is a flow chart, which schematically illustrates a method for inspection of bumps on a wafer, in accordance with an embodiment of the present invention. For the sake of convenience and clarity, the description that follows will refer to bump 40 on wafer 22, under inspection using elements of system 20, but the present method may similarly be applied in other systems and to other sorts of features. Although the steps of the method are described in a certain order, variations in this order are also possible, as will be apparent to those skilled in the art.

To find the required correction factors, optical microscope 35 is aligned precisely with X-ray beam 26 and captures an optical image of the bump array, at an optical imaging step 50. Microscope 35 captures an image of the area of the wafer under test, and analyzer 34 applies a pattern recognition algorithm to the image in order to identify the shapes and dimensions of the bumps, at an image processing step 52. Analyzer 34 also assesses the degree to which the area irradiated by the X-ray beam is covered by bumps neighboring the actual bump that is to be measured. For example, after acquiring an image from image sensor 36, analyzer 34 may apply color transformation and thresholding operations to convert the color or grayscale image to a binary representation. This binary image may be used in the numerical integration algorithm described below. A standard "blob analysis" function of the image processing package may be used to return the centroid coordinates of similar features within the field of view of the optical image.

Stage 23 translates wafer 22 so that the area that has been imaged by microscope 35 is located at the focus of X-ray beam 26. X-ray tube irradiates the area, and detectors 32 capture fluorescent X-rays 30 emitted from the area as a result. Analyzer 34 measures the fluorescence intensity as a function of energy, at an XRF measurement step 54.

Analyzer 34 computes the correction factors, $C_n$ and $C_s$, based on the results of image processing step 52, taking into account the X-ray beam size (irradiated area), bump dimensions and area coverage, at a correction computation step 56. The model typically assumes that the X-ray beam has a Gaussian profile, which is symmetrical about the center of the beam (taken as the origin of coordinates). It uses the bump diameter provided by the imaging processing results, as well as the bump height, which may be derived from user input or from automated three-dimensional measurements. As illustrated in FIGS. 3A and 3B, the bump height may be less than or greater than the bump radius, or it may be equal to the bump radius.

Analyzer 34 applies the correction factors in correcting the measured XRF intensity, in accordance with equation (1) above, at an intensity correction step 58. The corrected XRF gives an accurate indication of the actual height and composition of bump 40. Specifically, for example, if bump 40 comprises a certain metal, such as tin, and the XRF intensity $I^{measured}$ is measured for a specific emission line of the metal, then the corrected intensity $I_{sb}^{true}$, taken together with the measured bump diameter, will give an accurate value of the height and/or concentration of the metal in the bump.

Figure 5A:
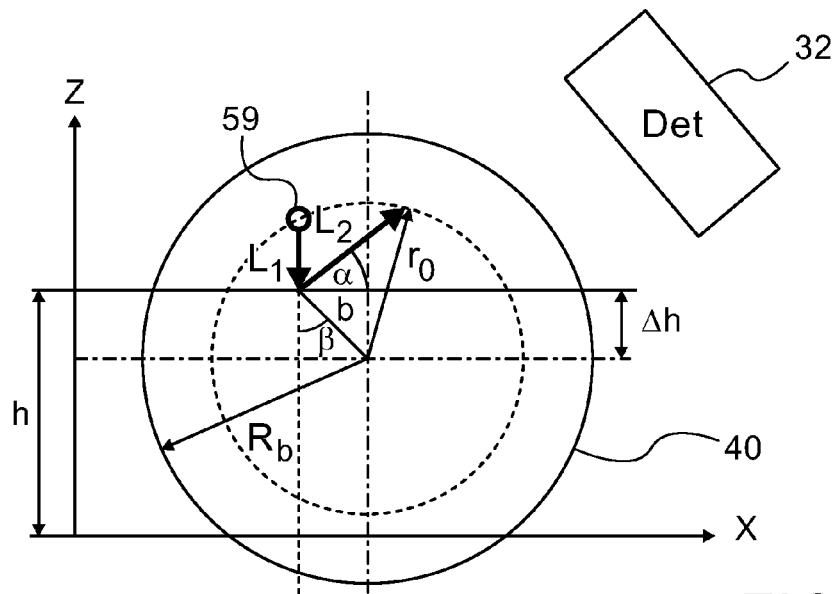
FIGS. 5A and 5B are schematic top and side views, respectively, of a micro-bump under inspection, illustrating geometrical parameters used in processing X-ray microfluorescence measurements, in accordance with an embodiment of the present invention.
Figure 5B:
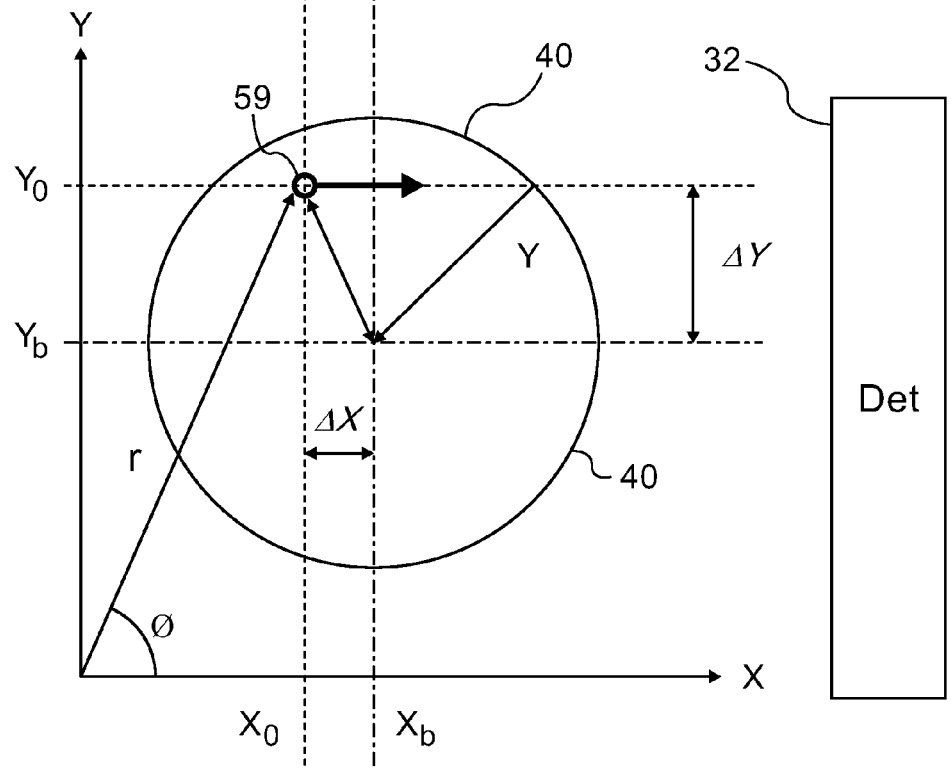

FIGS. 5A and 5B are schematic top and side views, respectively, of bump 40, illustrating geometrical parameters used in computing the correction factors at step 56. In this step, analyzer 34 integrates the expected XRF emission intensity over the area of the incident beam, using an (r, φ) coordinate system as shown in the figures. The computational model assumes that X-ray detector 32 is positioned to capture XRF emission at a certain angle. In practice, an array of such detectors is typically used, surrounding the array of bumps, and analyzer 34 takes the entire detector array into account.

The intensity of XRF emission for the single bump 40 shown in FIGS. 5A and 5B can be written as an integral in cylindrical coordinates as follows:

$$I = \frac{K}{2\pi\sigma^2} \int_0^{4\sigma} r \exp\left(-\frac{r^2}{2\sigma^2}\right) \int_0^{2\pi} \int_0^H \exp(-\mu_1 L_1) \exp(-\mu_2 L_2) \, dh \, d\varphi \, dr \quad (2)$$

This formula uses the following variables and values for each point 59 in the integration:

K [1/μm]—coefficient.
σ—X-ray beam width (FWHM/2.35) in μm.
μ1 and μ2—linear absorption coefficients for "input" and "output" X-ray paths respectively into and out of bump 40.
$L_1$ and $L_2$—"input" and "output" path lengths respectively.
h—height of current measurement point relative to wafer surface.
H—bump height.
r, φ—polar coordinates, wherein radius r=0 is at the center of the X-ray beam.

$L_1 = \text{sign} \cdot b \cos \beta + \sqrt{r_0^2 - b^2 \sin^2 \beta}$ $L_2 = \text{sign} \cdot b \sin(\alpha+\beta) + \sqrt{r_0^2 - b^2 \cos^2(\alpha+\beta)}$ $r_0^2 = R_B^2 - \Delta y^2, \; b = \sqrt{\Delta h^2 + \Delta x^2}, \; \Delta h = h + R - H$ $\Delta x = r \cos \varphi - x_b, \; \Delta y = r \sin \varphi - y_b, \; \beta = \arctan(\Delta x / \Delta h)$ $\text{sign} = (\Delta h < 0) ? (1 : -1)$.

$x_b$ and $y_b$—bump center coordinates.
α—detector slope.
Note that if $r_{cr}^2 = R_b^2 - \Delta h^2 < \Delta x^2 + \Delta y^2$, then the value of integral (2) will be zero.

In order to calculate the integral numerically for a single bump, a quadrature expression may be used:

$$I_{sb} = \frac{K \cdot \Delta h \Delta \varphi \Delta r}{2\pi\sigma^2} \quad (3)$$

-continued $$\sum_{i=0}^{I-1} r_i \exp\left(-\frac{r_i^2}{2\sigma^2}\right) \cdot \sum_{m=0}^{M-1} \sum_{j=0}^{J-1} \exp[-(\mu_1 L_{1i,j,m} + \mu_2 L_{2i,j,m})]$$

In this expression:

$\Delta r$=radius step (~1 um), $\Delta\phi$=phi step (~1 deg), $\Delta h$=bump height step (~1 um)

$L_1 = \text{sign} \cdot b_{i,m,j} \cos \beta_{i,m,j} + \sqrt{r_{0_{i,m}}^2 - b_{i,m,j}^2 \sin^2 \beta_{i,m,j}}$ $L_2 = \text{sign} \cdot b_{i,m,j} \sin(\beta_{i,m,j}+\alpha) + \sqrt{r_{0_{i,m}}^2 - b_{i,m,j}^2 \cos^2(\beta_{i,m,j}+\alpha)}$ $b_{i,m,j} = \sqrt{\Delta h_j^2 + \Delta x_{i,m}^2}$ $r_{0_{i,m}} = \sqrt{R_b^2 - \Delta y_{i,m}^2}$ $\Delta h_j = h_j + R_b - H$ $\Delta x_{i,m} = r_i \cos\phi_m - x_b, \Delta y_{i,m} = r_i \sin\phi_m - y_b$ $$\beta_{i,m,j} = \begin{cases} \frac{\pi}{2}, & \text{if } \Delta h_j = 0 \text{ and } \Delta x_{i,m} > 0 \\ \arctan\left(\frac{\Delta x_{i,m}}{\Delta h_j}\right), & \text{if } \Delta h_j \neq 0 \\ -\frac{\pi}{2}, & \text{if } \Delta h_j = 0 \text{ and } \Delta x_{i,m} < 0 \end{cases}$$

$I = \frac{R}{\Delta r}, M = \frac{360}{\Delta\phi}, J = \frac{H}{\Delta h}, r_i = \Delta r \cdot i + \frac{\Delta r}{2}, \phi_k = \Delta\phi \cdot k + \frac{\Delta\phi}{2}$ $h_j = \Delta h \cdot j + \frac{\Delta h}{2}$ $r_{crj} = \sqrt{R_B^2 - \Delta h_j^2}.$ Again, if $r_{0_{i,m}} > r_{crj}$, then the sum of formula (3) will be zero.

The above integration is carried out over all of the bumps falling within the X-ray beam to give the total intensity:

$$I_b = \sum_{n=1}^{N} I_{sb_n} \quad (4)$$

wherein $I_{sb}$=intensity of a single bump, and N=number of bumps. The resulting value $I_b$ gives the correction factor $$C_n = \frac{I_{sb}}{I_b},$$

which is applied to the measured XRF intensity as defined in equation (1) above in order to obtain values of bump height and material concentration that are quantitatively accurate for the current X-ray beam location and bump array geometry.

The factor $C_s$ is defined as:

$$C_S = \frac{I_f}{I_{sb}}$$

wherein $I_f$ is the fluorescence intensity for an infinite film, given by:

$$I_f = K \frac{1 - \exp[-H(\mu_1 + \mu_2/\sin\alpha)]}{\mu_1 + \mu_2/\sin\alpha}$$

If the bumps are cylindrical in shape, rather than spherical, the formulas above can still be used with the following changes:

$L_1 = H - h_j$ $$L_2 = \min\left(\frac{L_1}{\sin\alpha}, \frac{\Delta l}{\cos\alpha}\right)$$

$\Delta l = \sqrt{R_b^2 - \Delta y_{i,m}^2} - \Delta x_{i,m}$

If $\sqrt{\Delta x_{i,m}^2 + \Delta y_{i,m}^2} > R_b$, the sum of formula (3)=0.

Figure 6A:
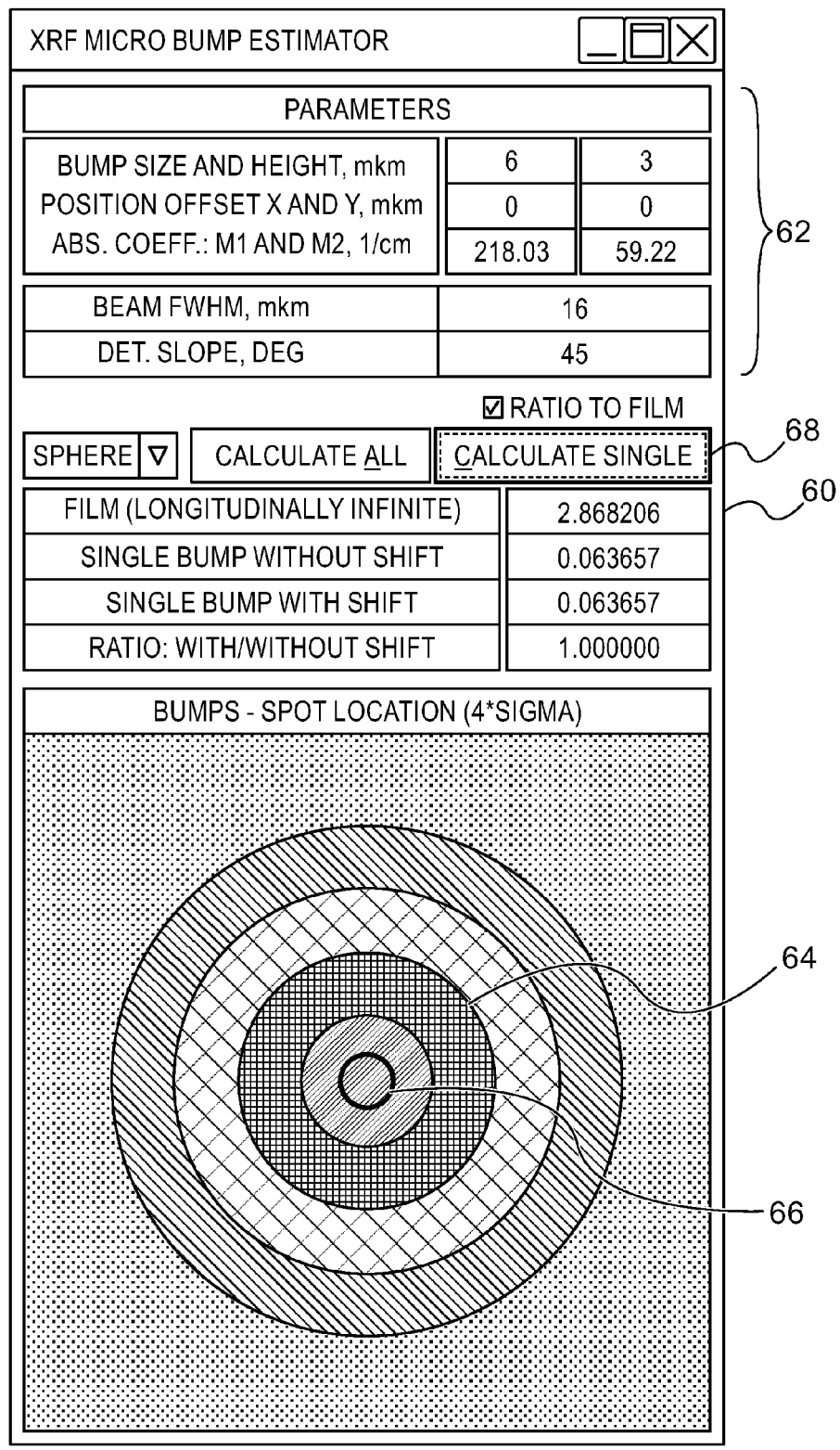
FIGS. 6A-6C are schematic representations of user interface screens in a program for extracting micro-bump properties from X-ray microfluorescence measurements, in accordance with an embodiment of the present invention.
Figure 6B:
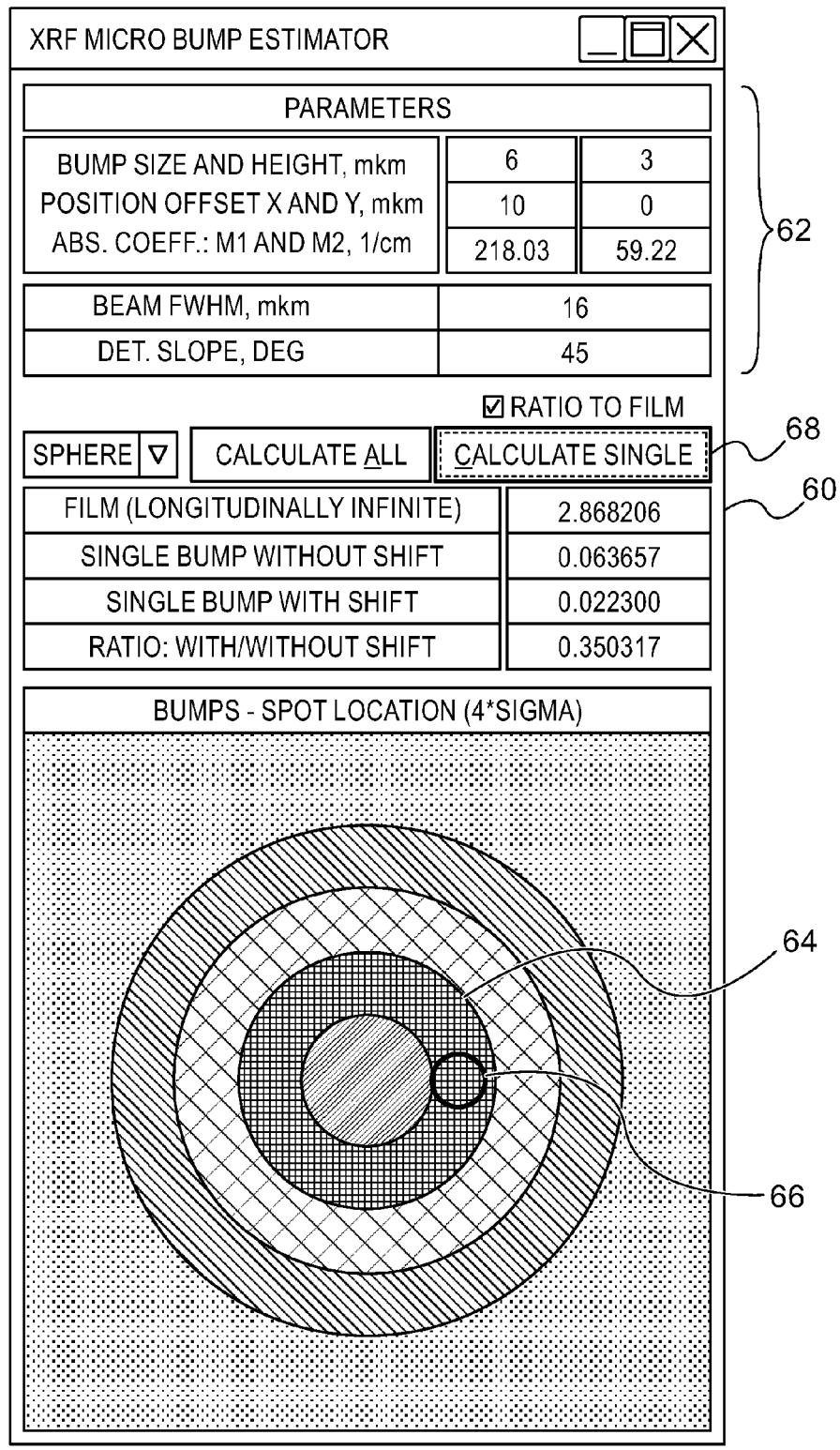
Figure 6C:
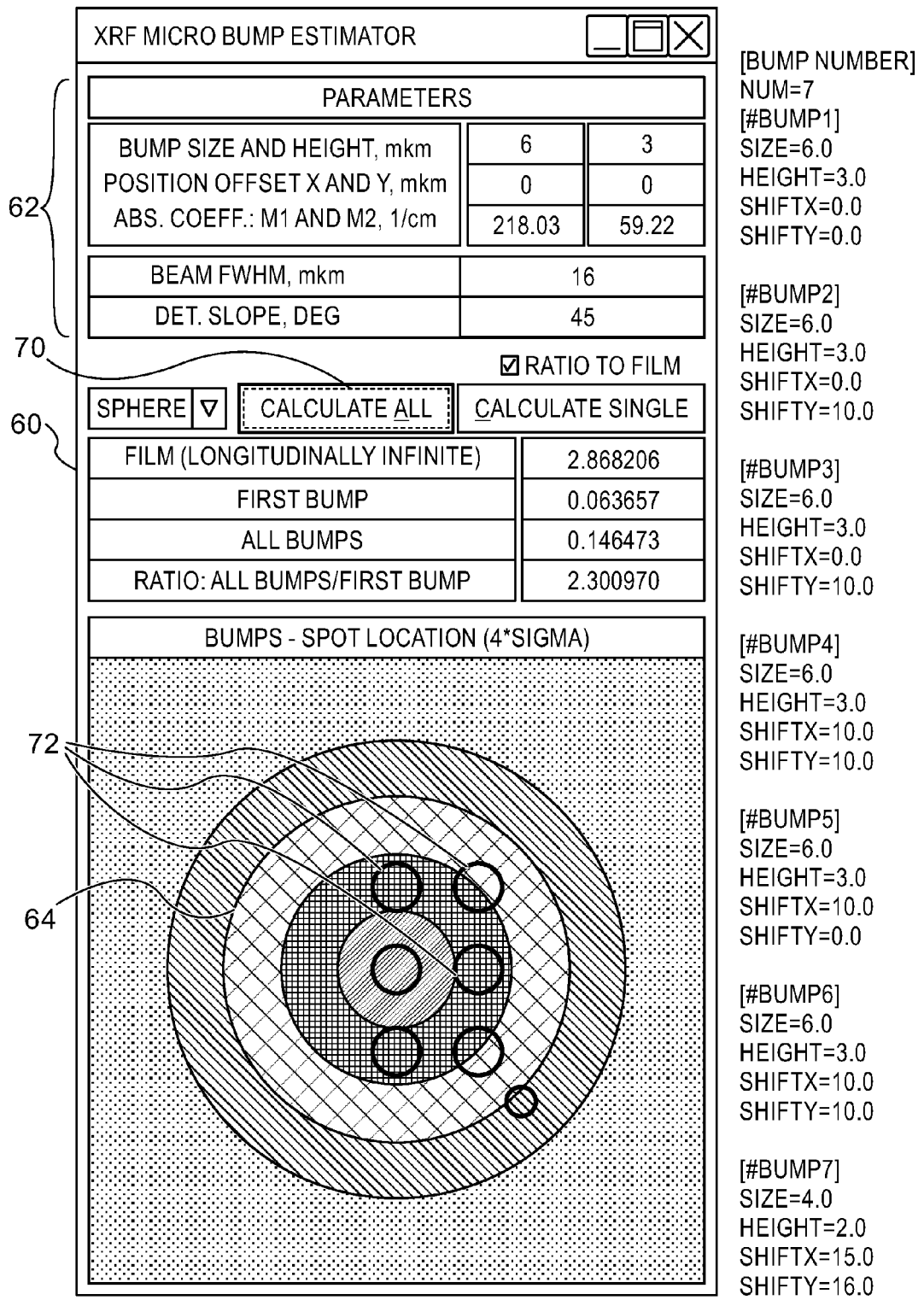

FIGS. 6A-6C are schematic representations of user interface screens 60 in a program for extracting bump properties from X-ray microfluorescence measurements, in accordance with an embodiment of the present invention. In an input section 62, the user is prompted to input known parameters of the bump in question, including size and height, offset relative to the X-ray beam center, X-ray absorption coefficients (for the irradiation and fluorescence wavelengths), X-ray beam size, and slope to the detector position. Alternatively, when system 20 is actually used in a foundry, at least some of these properties may be pre-programmed or estimated autonomously by analyzer 34 based on analysis of the optical image of the sample.

Screens 60 also show the location of the bump or bumps under inspection relative to an area 64 of X-ray beam 26. In FIGS. 6A and 6B, a single bump 66 is evaluated, wherein bump 66 is centered in area 64 in FIG. 6A and offset from the center in FIG. 6B. To calculate the correction factor in these cases, the user selects a "calculate single" button 68.

On the other hand, FIG. 6C shows an array of bumps 72, which are distributed over area 64. In this case, the user selects a "calculate all" button 70, whereupon analyzer 34 sums the intensities and computes the correction factors over the entire bump array. The correction factor in this case will enable analyzer 34 to extract the properties of the bump at the center of beam area 64 from the entire XRF signal that is received from all of bumps 72 together.

Although the embodiments described above relate specifically to measurement of bumps, the principles of the present invention may similarly be applied, mutatis mutandis, in measuring properties of other features, including not only protrusions (such as bumps), but also recesses in the surface of the sample. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for inspection, comprising:
   capturing an optical image of one or more features on a surface of a sample;
   irradiating an area of the sample containing at least one of the features with an X-ray beam;
   measuring an intensity of X-ray fluorescence emitted from the sample in response to the irradiating X-ray beam;

processing the optical image so as to extract geometrical parameters of the at least one of the features and to compute a correction factor responsively to the geometrical parameters; and applying the correction factor to the measured intensity in order to derive a property of the at least one of the features.

2. The method according to claim 1, wherein irradiating the area comprises focusing an X-ray beam onto the surface of the sample, and wherein the optical image is captured by a microscope that is aligned with the focused X-ray beam.

3. The method according to claim 1, wherein measuring the intensity of the X-ray fluorescence comprises detecting fluorescent X-rays using one or more detectors positioned at respective angles relative to the feature, and wherein processing the optical image comprises computing the correction factor responsively to respective angular slopes between the one or more detectors and the at least one of the features.

4. The method according to claim 1, wherein applying the correction factor comprises deriving at least one property of the at least one of the features, selected from a group of properties consisting of a composition and a size parameter of the at least one of the features.

5. The method according to claim 1, wherein processing the optical image comprises recognizing that the irradiated area of the sample contains a plurality of the features, and computing the correction factor so as to enable the property of a single feature to be derived from the intensity of the X-ray fluorescence that is received from the plurality of the features.

6. The method according to claim 1, wherein processing the optical image comprises recognizing that the at least one of the features has a shape that differs from a specified reference shape, and computing the correction factor so as to correct the intensity of the X-ray fluorescence for the shape of the at least one of the features.

7. The method according to claim 1, wherein processing the optical image comprises computing the correction factor by integrating an expected X-ray emission intensity over the irradiated area of the sample using the extracted geometrical parameters of the at least one of the features.

8. The method according to claim 1, wherein the sample is a wafer, and the features comprise bumps formed on the surface of the wafer, and wherein applying the correction factor comprises assessing a quality of the bumps.

9. Inspection apparatus, comprising:
- a microscope, which is configured to capture an optical image of one or more features on a surface of a sample;
- an X-ray source, which is configured to irradiate an area of the sample containing at least one of the features with an X-ray beam;
- one or more detectors, which are positioned to measure an intensity of X-ray fluorescence emitted from the sample in response to the irradiating X-ray beam; and
- a signal analyzer, which is configured to process the optical image so as to extract geometrical parameters of the at least one of the features, to compute a correction factor responsively to the geometrical parameters, and to apply the correction factor to the measured intensity in order to derive a property of the at least one of the features.

10. The apparatus according to claim 9, wherein the X-ray source comprises optics configured to focus the X-ray beam onto the surface of the sample, and wherein the microscope is aligned with the focused X-ray beam.

11. The apparatus according to claim 9, wherein the one or more detectors comprise multiple detectors, which are positioned at respective angles relative to the feature, and wherein the signal analyzer is configured to compute the correction factor responsively to respective angular slopes between the detectors and the at least one of the features.

12. The apparatus according to claim 9, wherein the signal analyzer is configured to derive at least one property of the at least one of the features, selected from a group of properties consisting of a composition and a size parameter of the at least one of the features.

13. The apparatus according to claim 9, wherein the signal analyzer is configured to recognize that the irradiated area of the sample contains a plurality of the features, and to compute the correction factor so as to enable the property of a single feature to be derived from the intensity of the X-ray fluorescence that is received from the plurality of the features.

14. The apparatus according to claim 9, wherein the signal analyzer is configured to recognize that the at least one of the features has a shape that differs from a specified reference shape, and to compute the correction factor so as to correct the intensity of the X-ray fluorescence for the shape of the at least one of the features.

15. The apparatus according to claim 9, wherein the signal analyzer is configured to compute the correction factor by integrating an expected X-ray emission intensity over the irradiated area of the sample using the extracted geometrical parameters of the at least one of the features.

16. The apparatus according to claim 9, wherein the sample is a wafer, and the features comprise bumps formed on the surface of the wafer, and wherein the signal analyzer is configured to apply the correction factor in assessing a quality of the bumps.

17. A computer software product, comprising a non-transitory computer-readable medium in which program instructions are stored, which instructions, when read by a computer, cause the computer to receive an optical image of one or more features on a surface of a sample and to receive a measurement of an intensity of X-ray fluorescence emitted from an area of the sample containing at least one of the features in response to an irradiating X-ray beam, and to process the optical image so as to extract geometrical parameters of the at least one of the features and to compute a correction factor responsively to the geometrical parameters, and to apply the correction factor to the measured intensity in order to derive a property of the at least one of the features.

* * * * *